United States Patent

Frey et al.

[11] Patent Number: 5,990,361
[45] Date of Patent: Nov. 23, 1999

[54] PROCESS FOR PRODUCING ETHYL TERTIARY BUTYL ETHER BY CATALYTIC DISTILLATION

[75] Inventors: Stanley J. Frey, Palatine; Scott P. Davis, Mount Prospect; Steven L. Krupa, Fox River Grove; Paul R. Cottrell, Arlington Heights, all of Ill.

[73] Assignee: UOP LLC, Des Plaines, Ill.

[21] Appl. No.: 09/099,162

[22] Filed: Jun. 18, 1998

Related U.S. Application Data

[60] Provisional application No. 60/053,382, Jul. 22, 1997.
[51] Int. Cl.⁶ ................................................. C07C 41/06
[52] U.S. Cl. ......................... 568/697; 568/694; 568/699
[58] Field of Search ..................................... 568/697, 694, 568/699

[56] References Cited

U.S. PATENT DOCUMENTS

| | | | |
|---|---|---|---|
| 4,198,530 | 4/1980 | Wentzeimer et al. | 568/697 |
| 4,413,150 | 11/1983 | Briggs | 568/697 |
| 5,158,652 | 10/1992 | Pucci et al. | 203/73 |
| 5,248,836 | 9/1993 | Bakshi et al. | 568/697 |
| 5,258,560 | 11/1993 | Marker | 568/697 |
| 5,368,691 | 11/1994 | Asselineau et al. | 203/29 |
| 5,401,887 | 3/1995 | Rastelli et al. | 568/697 |

Primary Examiner—Mukund J. Shah
Assistant Examiner—Pavanaram K Sripada
Attorney, Agent, or Firm—Thomas K. McBride; Frank S. Molinaro; Maryann Maas

[57] ABSTRACT

A low pressure catalytic distillation process for producing high purity ethyl tertiary butyl ether that contains less than 0.6 weight percent ethanol, and preferably less than 0.07 weight percent ethanol, has been developed. The high purity ethyl tertiary butyl ether is withdrawn directly from a catalytic distillation column. No downstream processing is necessary to remove excess ethanol from the ether product. A stream containing a significant amount of one or more inert azeotropic agents such as normal butane, isopentane, and isobutane is introduced along with the isobutylene and ethanol reactants into an etherification zone containing a catalytic distillation column. The catalytic distillation column is operated under low pressure conditions which result in the reaction of the ethanol with the isobutylene to form ethyl tertiary butyl ether. The inert azeotropic agent must be present at the inlet to the catalytic distillation column in an amount sufficient to azeotrope excess ethanol and cause the excess ethanol to distill into an overhead stream under the conditions of operation. The preferred azeotropic agent is isopentane. Excess ethanol forms an azeotrope with the azeotropic agent and is distilled with other hydrocarbons into an overhead stream. The ethyl tertiary butyl ether and no more than 0.6 weight percent ethanol are distilled into a bottoms stream and withdrawn directly from the catalytic distillation column.

6 Claims, No Drawings

PROCESS FOR PRODUCING ETHYL TERTIARY BUTYL ETHER BY CATALYTIC DISTILLATION

CROSS REFERENCE TO RELATED APPLICATION

This application claims priority of Provisional Application No. 60/053,382 filed Jul. 22, 1997.

BACKGROUND OF THE INVENTION

Ethers have become an important gasoline blending component in order to increase the octane rating of the gasoline without exceeding regulatory Reid vapor pressure limits and to reduce carbon monoxide emissions. Processes involving catalytic distillation have been used to produce ethers by the reaction of an alcohol with an isoalkene, see U.S. Pat. No. 5,258,560; in particular, catalytic distillation has been used to produce ethyl tertiary butyl ether by the reaction of ethanol and isobutylene. For example, U.S. Pat. No. 5,248,836 discloses passing an isobutylene-containing stream and a stream containing ethanol and ethyl tertiary butyl ether through a straight pass reactor to selectively react ethanol and a portion of the isobutylene to form a first product stream which is sent to a catalytic distillation column. In the catalytic distillation zone the ethyl tertiary butyl ether is largely distilled from the ethanol and isobutylene that are then further reacted to form a second product stream. The distilled ethyl tertiary butyl ether is collected and the second product stream is recycled to the straight pass reactor. U.S. Pat. No. 5,368,691 discloses a configuration for catalytic distillation whereby reaction zones are alternated with, and clearly separated from, distillation zones without a continuous liquid mass between a reaction zone and an adjacent distillation zone.

However, because excess ethanol is usually used to drive the etherification of isobutylene to high conversion and the unreacted ethanol distills with the product ethyl tertiary butyl ether, it is difficult to obtain a catalytic distillation product ethyl tertiary butyl ether having low levels of ethanol. Removing the ethanol from the ethyl tertiary butyl ether product results in a product having a lower Reid vapor pressure which, in turn, makes the ether product more valuable. U.S. Pat. No. 5,158,652 discloses a process for separating ethyl tertiary butyl ether and ethanol using two distillation columns operating at different temperatures and pressures. U.S. Pat. No. 5,401,887 discloses a process where the reactants undergo etherification in a reactor and the reactor effluent is sent to a distillation column for separation. The distillation column bottoms containing both ethanol and ethyl tertiary butyl ether is further processed to separate the ethanol from the ethyl tertiary butyl ether by adsorbing the ethanol on a selective adsorbent. U.S. Pat. No. 4,198,530 discloses a process for producing methanol-free methyl tertiary butyl ether. The methyl tertiary butyl ether is formed in an etherification reactor using a feed that contains methanol, $C_4$ hydrocarbons, and a significant amount of normal butene. The reactor effluent is passed to a distillation zone where substantially all of the methanol in the effluent is azeotropically removed together with the $C_4$ hydrocarbons and whereby substantially all of the methanol is removed from the methyl tertiary butyl ether. U.S. Pat. No. 4,413,150 discloses converting isobutylene and an alcohol to an ether in a reactor and then separating the product ether from the reaction mixture in a single distillation column where the product ether is substantially free of $C_4$ hydrocarbons and alcohol.

Applicants, however, are the first to realize that in a low pressure catalytic distillation process, by routing a stream containing at least one inert azeotropic agent to an etherification zone at a point prior to the low pressure catalytic distillation column, excess ethanol will be drawn into an azeotrope with the inert azeotropic agent and will not be able to contaminate the ethyl tertiary butyl ether product. The result is a high purity ethyl tertiary butyl ether product containing no more than 0.6 weight percent ethanol available directly from the catalytic distillation column. No further downstream processing is needed for removal of ethanol and purification of the ethyl tertiary butyl ether.

SUMMARY OF THE INVENTION

The purpose of the invention is to provide a low pressure catalytic distillation process for producing high purity ethyl tertiary butyl ether that contains less than 0.6 weight percent ethanol, and preferably less than 0.07 weight percent ethanol. The high purity ethyl tertiary butyl ether is withdrawn directly from a catalytic distillation column. No downstream processing is necessary to remove excess ethanol from the ether product. A stream containing one or more inert azeotropic agents selected from the group consisting of normal butane, isobutane, and isopentane is introduced along with the isobutylene and ethanol reactants into an etherification zone containing a catalytic distillation column operated under low pressure conditions. The reaction of the ethanol with the isobutylene forms ethyl tertiary butyl ether. The inert azeotropic agent must be present at the inlet to the catalytic distillation column in an amount sufficient to azeotrope excess ethanol and cause the excess ethanol to distill into an overhead stream under the conditions of operation. The preferred azeotropic agents are isopentane and normal butane. Excess ethanol forms an azeotrope with the azeotropic agent and is distilled with other hydrocarbons into an overhead stream. The ethyl tertiary butyl ether and no more than 0.6 weight percent ethanol are distilled into a bottoms stream and withdrawn directly from the catalytic distillation column.

DETAILED DESCRIPTION OF THE INVENTION

The present invention provides a process for producing an ethyl tertiary butyl ether stream that contains no more than 0.6 weight percent ethanol, and preferably 0.07 weight percent ethanol, by introducing a stream containing sufficient amounts of one or more inert azeotropic agents along with the ethanol and isobutylene reactants to an etherification zone containing a low pressure catalytic distillation column. The etherification zone also preferably contains at least one fixed bed reactor connected in series to the catalytic distillation column, and the most preferred etherification zone contains two serially-connected fixed bed reactors followed by one catalytic distillation column. The fixed bed reactors are used to perform a large portion of the etherification reaction and the catalytic distillation column allows for conversion beyond that which is achievable in a static system limited by equilibrium. Fixed bed reactors and catalytic distillation are known techniques for the production of ethers, and catalytic distillation involves one or more distillation zones and one or more reaction zones, all located within the same vessel. The distillation zones typically contain distillation structures such as inert packings or distillation trays. The reaction zones contain catalyst capable of catalyzing the etherification reaction and distillation structure for the distillation of components within the reaction zone. The exact fixed bed and catalytic distillation configurations used are not critical to this invention; any known catalytic distillation configuration for the formation of ethers may be used in the practice of this invention. Similarly, the catalyst used in the fixed bed and catalytic distillation columns may be any catalyst known to catalyze the etherification reaction including divinylbenzene cross-linked polystyrene ion exchange resins in which the active sites are sulfonic acid groups, and inorganic heterogeneous catalysts such as boric acid, bismuth molybdate, and metal salts of phosphomolybdic acids wherein the metal is lead, antimony, tin, iron, cerium, nickel, cobalt, or thorium. Boron phosphate, blue tungsten oxide, and crystalline aluminosilicates of the zeolitic molecular sieve type have also been proposed as heterogeneous catalysts for the reaction of ethanol and isobutylene. The conditions at which the fixed bed reactors are operated are well known and include pressures ranging from about 150 to about 250 psig and temperatures ranging from about 35° C. to about 75° C. Conditions for the catalytic distillation unit are also known and include pressures ranging from about 80 to about 120 psig. Note that in the catalytic distillation column the conditions are limited to those compatible with the catalyst used and are therefore of a more narrow range as compared to a conventional distillation column. Specifically, the catalytic distillation column is restricted to operation at a lower pressure in order to control the temperature in the reaction portion. A conventional distillation column may be operated at higher pressure to increase the amount of azeotropic ethanol in the column overhead.

Isobutylene and ethanol reactants are introduced to the etherification zone. The reactants may be obtained from any source. The isobutylene is typically in a stream that also contains other $C_4$ hydrocarbons. A common source of isobutylene is a light hydrocarbon catalytic dehydrogenation process such as the preferred Oleflex process. The effluent of the light hydrocarbon catalytic dehydrogenation operation is a mixed $C_4$ stream that includes isobutylene, normal butane, isobutane, butene-1, trans-butene-2 and cis-butene-2. The isobutylene is usually present in an amount ranging from about 10 to about 70 mole percent of the mixed $C_4$ stream. It is contemplated that some propane and propylene may also be present. A common source of ethanol is the fermentation of grain. A greater than stoichiometric amount of ethanol is introduced to the etherification zone in an effort to increase the conversion of isobutylene. As the isobutylene and ethanol contact the catalyst in the fixed bed reactors, the etherification reaction is catalyzed and ethyl tertiary butyl ether is formed. Due to equilibrium limitations, not all of the isobutylene will be consumed and the effluent of the fixed bed reactors contains isobutylene, ethanol, ethyl tertiary butyl ether, trace byproducts and other unreacted hydrocarbons. To react the remaining isobutylene, the effluent is introduced to the catalytic distillation column.

In the catalytic distillation column the isobutylene and ethanol contact the catalyst and further etherification is catalyzed. As ethyl tertiary butyl ether is formed, it is rapidly distilled and removed from the reactants, thereby facilitating the continuation of the etherification reaction. The product ether is distilled into a bottoms stream and removed from the catalytic distillation column. Most of the other components are distilled into an overhead stream and removed from the catalytic distillation column. A small amount of a few byproducts may distill into the bottoms stream. However, a problem arises due to fact that of the typical products present, ethanol has the highest pure component boiling point and by distillation alone would distill into the ether-containing bottoms stream. The ethanol present in the ether product stream decreases the purity of the ether product, and in order to take full advantage of the low blending Reid vapor pressure of the ethyl tertiary butyl ether product, the ethanol contaminant should be no greater than a 0.6 weight percent of the product. It is also contemplated that the blending octane number of the product ethyl tertiary butyl ether will be higher when the ethanol contaminant is kept to a minimum. Removal of the ethanol contaminant by techniques such as water extraction, stripping, or adsorption is difficult and costly, and the better approach is to minimize the amount of ethanol contamination occurring in the catalytic distillation column rather than attempt to further process the ether product stream to remove ethanol. Unfortunately, increasing the catalytic distillation column pressure to improve the distillation is of limited use since the distillation column also contains catalyst, and the limitations of the catalyst dictate the range of operating conditions.

Therefore, the present invention requires that a stream containing at least one inert azeotropic agent also be introduced to the etherification zone. Specific agents are discussed at length below. The azeotropic agent is introduced to the etherification zone at a point prior to the catalytic distillation column and preferably after the fixed bed reactors. It is possible to introduce the azeotropic agent at the same location as the reactants, but that is less preferred since the volume is then increased at a portion of the etherification zone where the azeotropic agent is unnecessary. Ordinarily, introducing a significant volume of inert material to a reaction would not be expected to result in increased product purity. Flowing large volumes of inert material through a reaction zone is generally considered to be undesirable as the complete physical structure of the reaction zone must be enlarged to flow the combined volume of reaction mixture and inert material. Correspondingly, the costs of constructing and operating the physically enlarged reaction zone are increased in order to handle the increased total volume. However, in the low pressure catalytic distillation column described above, it is extremely beneficial to introduce a large amount of inert azeotropic agent.

Specifically, by requiring the independent stream containing an inert azeotropic agent to be introduced to the catalytic distillation column, virtually all of the excess ethanol is incorporated into an azeotrope with the inert azeotropic agent and other inert hydrocarbons present and is carried from the catalytic distillation column in the overhead stream thereby leaving little ethanol to contaminate the bottoms ethyl tertiary butyl ether product stream. The bottoms ethyl tertiary butyl ether product stream is of increased purity and contains less than 0.6 weight percent ethanol contaminant.

The azeotropic agents are inert alkanes containing 4 or 5 carbon atoms that have the capacity to azeotrope with ethanol under the catalytic distillation conditions. The term "inert" is meant to indicate that the azeotropic agents will not react to form appreciable amounts of byproduct in the fixed bed reactors or in the catalytic distillation column as described herein. Specific azeotropic agents include isopentane, normal butane, and isobutane. The preferred agents are those able to incorporate a higher amount of ethanol into an azeotrope at the operating conditions of the catalytic distillation column. The preferred agents are isopentane and normal butane with isopentane being the most preferred. The agents may be obtained from any source including, for example, by distillation of a crude $C_4$ stream, fluidized catalytic cracking, steam cracking, and gas separation plants.

One or more agents may be used, and the amount of agent necessary is dependent on several factors. First, the amount of ethanol that is able to azeotrope with each individual agent is different. For convenience, the term "ethanol capacity" will be used to refer to a characteristic of the azeotropic agent defined by that amount of ethanol that is drawn into an azeotrope with the individual azeotropic agent. Secondly, within a single agent the ethanol capacity varies with pressure. Thirdly, the amount of agent is dependent upon the desired purity of the ether product stream and the isobutylene conversion achieved. Therefore, the amount of overall agent necessary is determined by the weighted sum of the ethanol capacities for each agent used, where the ethanol capacity for each agent is determined by the pressure of operation, with the sum then being used in correlation with the amount of excess ethanol in the catalytic distillation column and the desired purity of the ether product. This determination is best described by examples.

The first examples are those where the azeotropic agent is a single component. Isopentane and normal butane are particularly preferred as the azeotropic agents due to the large amount of ethanol incorporated into an ethanol-isopentane or ethanol-normal butane azeotrope. For example, at 85 psig, an ethanol-isopentane azeotrope would contain about 14 mass percent ethanol, an ethanol-normal butane azeotrope would contain about 2.5 mass percent ethanol, while an isobutane-ethanol azeotrope would contain only 0.5 mass percent ethanol. This comparatively large azeotropic capacity for ethanol in combination with an overall large concentration of isopentane or normal butane introduced to the catalytic distillation column causes the unreacted ethanol to form an isopentane-ethanol or normal butane-ethanol azeotrope and therefore would be unable to distill into the ethyl tertiary butyl ether bottoms stream. The isopentane-ethanol or normal butane-ethanol azeotrope is distilled along with other $C_4$ hydrocarbons into the overhead stream of the catalytic distillation column leaving the ethyl tertiary butyl ether product stream with no more than 0.6 weight percent ethanol. As discussed above, the amount of azeotropic agent to be added depends on the ethanol capacity of the azeotropic agent, the operating pressure, the amount of excess ethanol present in the catalytic distillation column, and the desired purity of the ether product. In general, to achieve an ether product containing less than 0.6 weight percent ethanol when isopentane is used as the sole azeotropic agent, the isopentane must be present in a weight ratio ranging from about 5:1 to about 8:1 with the ethanol at the overhead from a catalytic distillation column designed to operate in the about 90 to about 120 psig range. When normal butane is used as the sole agent, the normal butane must be present in a weight ratio ranging from about 30:1 to about 50:1 with the ethanol at the overhead from the catalytic distillation column designed to operate in the about 90 to about 120 psig range. When isobutane is used as the sole agent, the isobutane must be present in a weight ratio ranging from about 124:1 to about 450:1 with the ethanol at the overhead from the catalytic distillation column designed to operate in the about 90 to about 120 psig range. All the above ratios apply when the reactors, both fixed bed and catalytic distillation, are operating at design conversions for isobutylene. Should actual conversions fall outside of design expectations, the ratio of azeotropic agent to ethanol required may lie outside the above described ranges.

When the azeotropic agent is a combination of two or more components, the determination of the quantity needed becomes more complex. A specific example of such a determination is as follows: the ether product is to contain no more than 0.07 weight percent ethanol, the catalytic distillation column is operating at 85 psig, and the reactants are introduced to the catalytic distillation column at a rate of 1000 kg/hr ethanol and 867 kg/hr isobutylene. These rates result in a 1.44:1 molar ratio of ethanol to isobutylene and the desired conversion of isobutylene is 99.0 weight percent. The azeotropic agent is a combination of 80 weight percent normal butane and 20 weight percent isobutane. At 85 psig, an ethanol-normal butane azeotrope would contain about 2.5 mass percent ethanol and an isobutane-ethanol azeotrope would contain only 0.5 mass percent ethanol. From these specifics an algebraic equation can be solved to determine that the azeotropic agent stream is introduced to the catalytic distillation column at 19,458 kg/hr. An example of a suitable equation is: the flowrate of excess ethanol=(the amount of compound 1 in the azeotropic agent stream) (R) (the ethanol capacity of compound 1 at the specified conditions)+(the amount of compound 2 in the azeotropic agent stream) (R) (the ethanol capacity of compound 2 at the specified conditions). Solving for R provides the flowrate of the stream containing the combination of components. The equation above is only one example of the many ways the flowrate of the azeotropic agent stream may be determined.

In another example of a combination azeotropic agent stream, where the conditions, percent conversion, and product purity are the same as in the above combination azeotropic agent stream example, again reactants are introduced to the catalytic distillation column at a rate of 1000 kg/hr ethanol and 867 kg/hr isobutylene. However, in this example the azeotropic agent is combination of 50 weight percent normal butane and 50 weight percent isopentane. At 85 psig, an ethanol-normal butane azeotrope would contain about 2.5 mass percent ethanol and an isopentane-ethanol azeotrope would contain about 14 mass percent ethanol. Therefore, the azeotropic agent stream is introduced to the catalytic distillation column at 4,541 kg/hr.

For complex systems involving multiple azeotropic agents, determinations of the quantity of each azeotropic agent needed to remove the desired amount of ethanol from the ether product are best accomplished using commonly available process simulation software such as Hysys available from Hyprotech Ltd. and Aspen Plus available from Aspen Technologies, Inc. Manual calculations using established engineering procedures and known azeotropic characteristics, such as found in Holderbaum, T.; Utzig, A.; GMehling, *J. Fluid Phase Equilibria,* 1991, 63, 219–226; and Lecat, M. *Ann. Soc. Sci. Bruxelles,* 1929, 49B/I, 34 may be successfully performed, but would be labor intensive and therefore not recommended.

Another factor to consider in determining the necessary quantity of azeotropic agent is that the compositions of isobutylene containing streams may vary, and some compositions may contain compounds that form an azeotrope with ethanol. In this case, the amount of additional azeotropic agent that must be added to the catalytic distillation column may be reduced to account for the azeotropic capacity of the compounds already present in the isobutylene containing stream.

The ethyl tertiary butyl ether product stream having no more than 0.6 weight percent ethanol can be collected and used in, for example, gasoline blending without further processing. The overhead stream may be treated to conserve and recycle components.

What is claimed is:

1. A low pressure catalytic distillation process for producing an ethyl tertiary butyl ether stream containing less than 0.6 weight percent ethanol comprising:

a) introducing ethanol, isobutylene, and a stream containing at least one inert azeotropic agent selected from the group consisting of normal butane, isobutane, isopentane, and a combination thereof to an etherification zone having a catalytic distillation column that contains an etherification catalyst and operates at a pressure ranging from about 80 to about 120 psig, said inert azeotropic agent(s) being introduced to the catalytic distillation column in amounts sufficient to form an azeotrope with unreacted ethanol and thereby provide an ethyl tertiary butyl ether product stream containing no more than 0.6 weight percent ethanol and an overhead stream containing an azeotrope of ethanol and inert azeotropic agent(s);

b) removing the ethyl tertiary butyl ether product stream containing less than about 0.6 weight percent ethanol from the catalytic distillation column; and c) removing the overhead stream from the catalytic distillation column.

2. The process of claim 1 wherein the inert azeotropic agent is normal butane which is introduced in an amount sufficient to provide a weight ratio in the range of from about 30:1 to about 50:1 of normal butane to ethanol measured at the overhead stream from the catalytic distillation column.

3. The process of claim 1 wherein the inert azeotropic agent is isopentane which is introduced in an amount sufficient to provide a weight ratio in the range of from about 5:1 to about 8:1 of normal butane to ethanol measured at the overhead stream from the catalytic distillation column.

4. The process of claim 1 wherein the ethyl tertiary butyl ether product stream contains less than about 0.07 weight percent ethanol.

5. The process of claim 1 wherein the etherification zone contains at least one fixed bed reactor serially connected to at least one catalytic distillation column.

6. The process of claim 5 wherein the stream containing at least one inert azeotropic agent is introduced to the etherification zone at a point after the fixed bed reactor and before the catalytic distillation column.

* * * * *